(12) United States Patent
Oishi et al.

(10) Patent No.: US 6,685,671 B1
(45) Date of Patent: Feb. 3, 2004

(54) BALLOON CATHETER FOR PUNCTURING, MEDICAL TUBE INTRODUCTION DEVICE USING THE CATHETER AND METHOD FOR USE THEREOF

(75) Inventors: Hideto Oishi, 203 I.V.Y. Garden, 2-30, Mihara 1-chome, Asaka-shi, Saitama 351-0025 (JP); Minoru Shibata, Akita (JP); Yukihiko Sakaguchi, Akita (JP)

(73) Assignees: Sumitomo Bakeleite Co., Ltd., Tokyo (JP); Hideto Oishi, Saitama (JP)

( * ) Notice: Subject to any disclaimer, the term of this patent is extended or adjusted under 35 U.S.C. 154(b) by 0 days.

(21) Appl. No.: 09/380,837

(22) PCT Filed: Jan. 14, 1999

(86) PCT No.: PCT/JP99/00110
§ 371 (c)(1),
(2), (4) Date: Sep. 10, 1999

(87) PCT Pub. No.: WO99/36120
PCT Pub. Date: Jul. 22, 1999

(30) Foreign Application Priority Data

Jan. 14, 1998 (JP) ............................................ 10-017994

(51) Int. Cl.[7] .......................... A61M 29/00; A61M 1/00; A61M 37/00
(52) U.S. Cl. .......................... 604/96.01; 604/27; 604/48
(58) Field of Search .................. 604/28, 27, 96.01, 604/48, 103.06, 97.01, 97.03, 98.01, 103.08, 103.11, 104, 910, 915–920, 514, 516, 164.13; 606/196, 191–192; 600/433, 434

(56) References Cited

U.S. PATENT DOCUMENTS

| | | | |
|---|---|---|---|
| 3,983,879 A | * 10/1976 | Todd ............................ 604/915 |
| 4,384,584 A | * 5/1983 | Chen ............................ 604/28 |
| 4,697,595 A | * 10/1987 | Breyer et al. ................. 128/660 |
| 4,899,747 A | * 2/1990 | Garren et al. ................. 606/192 |
| 5,330,500 A | * 7/1994 | Song ............................ 606/198 |
| 5,344,400 A | * 9/1994 | Kaneko et al. ................. 604/96 |
| 5,423,742 A | * 6/1995 | Theron .......................... 604/28 |
| 5,478,320 A | * 12/1995 | Trotta .......................... 604/96 |
| 5,499,625 A | * 3/1996 | Frass et al. .............. 128/200.26 |
| 5,520,641 A | * 5/1996 | Behnke et al. ................. 604/86 |
| 5,624,430 A | * 4/1997 | Eton et al. ...................... 604/1 |
| 5,769,819 A | * 6/1998 | Schwab et al. ............. 604/103 |
| 5,968,012 A | * 10/1999 | Ren et al. .................... 604/103 |
| 6,106,517 A | * 8/2000 | Zupkas ......................... 606/20 |
| 6,210,364 B1 | * 4/2001 | Anderson et al. ........ 604/96.01 |
| 6,270,504 B1 | * 8/2001 | Lorentzen Cornelius et al. 606/108 |

* cited by examiner

Primary Examiner—Jeffrey R. Jastrzab
Assistant Examiner—Leslie Deak
(74) Attorney, Agent, or Firm—Duane Morris LLP

(57) ABSTRACT

A medical tube inserting device that ensures safely and infallibly a route for draining of digestive juices and infusion of drug solutions, enteral nutrition and the like, and more specifically, a balloon catheter for puncturing which does not rupture that ensures a safe and infallible rout for infusion of a enteral nutrition solution and the like. The tube inserting device containing this catheter, and a method for use thereof. The route can be percutanelosly made safe and sure in all tubular organs like the esophagus, stomach, bile duct, pancreatic duct, intestine, urinary duct, and urinary bladder by a balloon catheter for puncturing, equipped with a balloon which does not rupture by puncturing, and an ultrasonic probe, a puncturing needle a guide wire, a dilator, a sheath and an indwelling catheter.

10 Claims, 5 Drawing Sheets

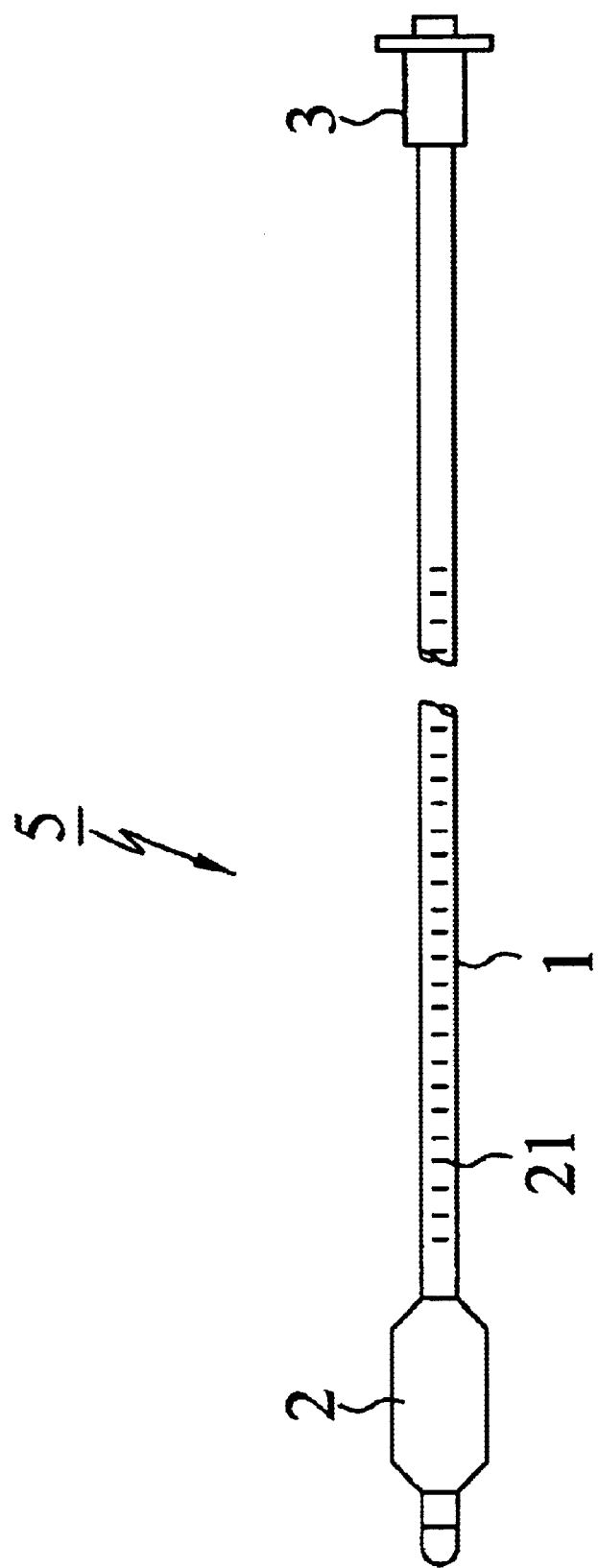

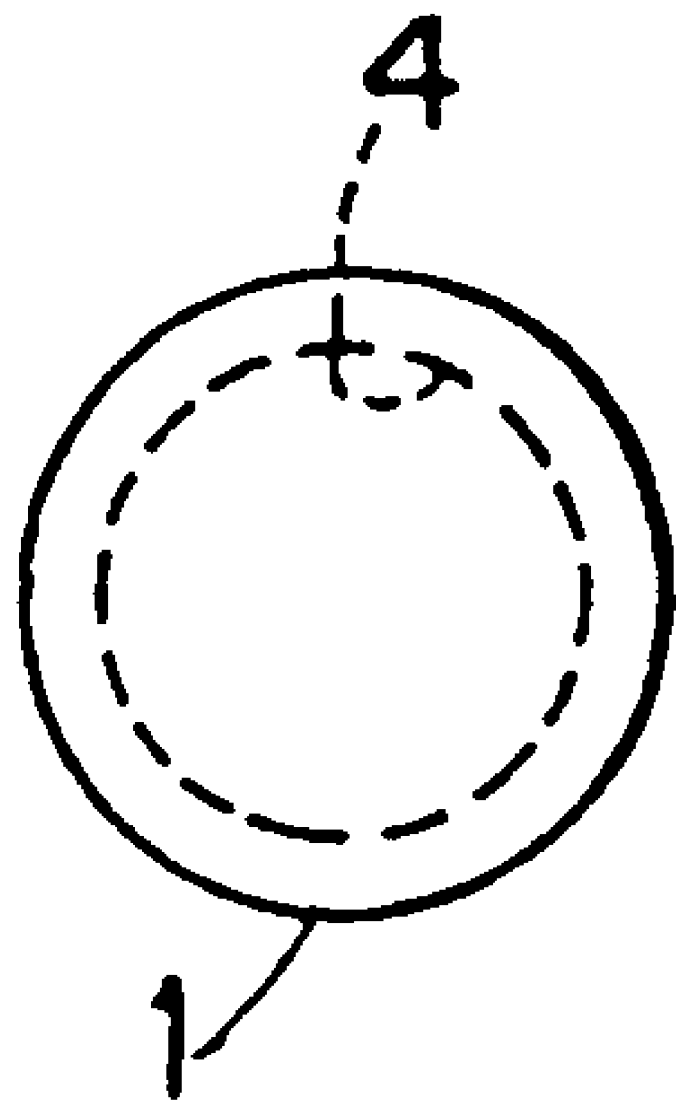

BEFORE BALLOON EXPANSION

AFTER BALLOON EXPANSION (IN ULTRASONIC PROBE PUSH)

BALLOON CATHETER FOR PUNCTURING, MEDICAL TUBE INTRODUCTION DEVICE USING THE CATHETER AND METHOD FOR USE THEREOF

TECHNICAL FIELD OF THE INVENTION

The present invention relates to a medical tube inserting device for ensuring safely and infallibly a route for drainage of digestive juices and infusion of drug solution, enteral nutrition and the like, and particularly, a balloon catheter for puncturing endowed with a function so that it does not rupture immediately by puncturing thereby ensuring lumen, and structures of tube inserting devices including the above-described catheter and a method for use thereof.

BACKGROUND OF THE INVENTION

Conventionally, particularly as a method for enteral nutrition dosage, a pediatric surgeon Gaudert and an endoscope surgeon Ponsky developed percutaneous endoscopic gastrostomy (PEG) in 1979 which is an endoscopic surgery for forming fistula opening on the surface of lumen of stomach and abdominal wall skin using an endoscope (Japanese Patent Application National Publication Laid-Open No. 6-503243), further, some technologies for applying this technology have been developed and are in widespread use. However, this is not to mention that this technology is restricted to doctors who can handle an endoscope. Also, this technology is restricted by cases and can not be used or use thereof is difficult in cases such as "when massive ascites are stored", "when liver and transverse colon are present between stomach and abdominal wall", "after a gastrectomy," and the like since stomach walls and abdominal walls are needled.

Further, there is a method with a nasal gastric tube; however, when indwelling lasts for a long period of time, pain in naris, nasal cavity and pharynx may increase and ulcers may be formed in the naris which makes continuous indwelling difficult, and further, pneumonia may even coincide due to difficulty of expectoration.

The method is also not preferable from these standpoints in view of QUALITY OF LIFE.

Further, in 1983, Allem. S. Chen et al. have suggested in the United States a method in which a bulb or optical fiber or magnet is installed in a balloon, a tube equipped with the balloon is inserted via nose, a cervical area is needled using a detector for detecting transmitted light or magnetic wave at the cervical area, and an esophagostomy is made for indwelling of a nutrition tube. In Japan, Nakano et al. developed a method for making an esophagostomy under X-ray fluoroscopy in 1993. In this indwelling method, a tube equipped with a balloon is inserted into an esophagus via the nose, a contrast medium is injected into the balloon in the cervical esophagus to expand lumen of the cervical esophagus, then, the cervical esophagus is needled percutaneously under X-ray fluoroscopy, and an esophagostomy is made for indwelling of a nutrition tube. The indwelling method of Nakano is simple, imparts minimal invasion and pain to patients and is useful for nutrition control for a long period of time, however, in this method, puncturing is conducted only under X-ray fluoroscopy and there is a possibility of danger in view of the anatomical structure of cervix. Further, in any of the suggested two methods, a balloon catheter is used having a tube equipped with a balloon which ruptures when punctured; therefore, in the puncturing, whether the puncturing needle reaches the esophagus lumen or not is determined by the puncturing of the balloon, and there is a danger that the leading point of the needle, after puncturing, injures the esophageal wall or the puncturing needle releases from the esophageal wall due to the esophagus collapsing.

On the other hand, the present inventor Oishi et al. improved the method of Nakano et al. in which a an esophagostomy is formed under X-ray fluoroscopy, and invented, as a method for needling a balloon of a balloon catheter, a method in which a balloon is needled with a puncturing needle safely and infallibly while externally confirming position of the balloon using a ultrasonic probe ("Regarding Percutaneous Trans-esophageal Gastro-tubing, Application and Utility Thereof", Journal of Japan Surgical Society, 1997. "Regarding Esophageal Gastro-tubing, Knack and Side-injury Percutaneous Trans Thereof", The Japanese Journal of Gastroenterological Surgery, 1997.). However, in this method, the danger that the leading point of the needle after puncturing of the balloon injures the esophageal wall or the puncturing needle releases from the esophageal wall remains, since a Foley catheter which causes rupture by puncturing is used similar to the method of Nakano.

The present invention has been made in view of the above-described conditions, and the object thereof is to provide a medical tube inserting device for ensuring safely and infallibly a route for drainage of digestive juices and infusion of drug solution, enteral nutrition and the like, and more specifically, a balloon catheter for puncturing having no danger that the leading point of a needle injures the esophageal wall and the like or the puncturing needle releases from the esophageal wall and the like, a medical tube inserting device using this catheter, and a method for use thereof.

DISCLOSURE OF THE INVENTION

Namely, the balloon catheter for puncturing of the present invention provided an intending solution of the above-described problems is a balloon catheter for puncturing which is inserted through a puncture area in a body via nose and the like, expanded by fluid such as physiological saline and the like and needled, wherein the above-described balloon is so constituted that when it is needled externally by a puncturing needle, it does not rupture immediately and lumen can be ensured. More specifically, the balloon has a thickness of 0.01 to 1 mm, a tensile strength of 8 to 25 MPa, a tear strength of 20 to 60 kg/cm, a 100% modulus of 3 to 6 MPa, an elongation of 300 to 460% and a balloon internal pressure of 2.8 to 75 psi, and does not rupture immediately in needling by a puncturing needle; and a catheter shaft made of a material having remarkably different levels of ultrasound transmission as compared with internal fluid such as physiological saline and the like in the balloon is placed approximately in the center of lumen of the balloon; in addition, for improvement of insertion operation, lumen is provided so that the balloon catheter can be inserted smoothly into a hollow organ along a previously inserted guide wire or a stilet is contained for firming a catheter up; further, for enabling insertion operation without X-ray contrast, graduation is provided on the catheter shaft and a pilot balloon for confirming expansion of the balloon is placed in the vicinity of a connector area.

Owing to the above-described constitution, when a catheter of the present invention is used, a catheter shaft having excellent visibility is situated in the center of the balloon in an ultrasonic echo image in needling; therefore, by adjusting puncturing predetermined lines onto the above-described echo image, not only is simple puncturing enabled but also the above-described balloon does not rupture immediately when punctured; consequently, a danger that a needle injures puncture areas or a needle releases from the puncture areas almost disappears.

In the present invention, the medical tube inserting device provided an intending solution of the above-described, prior art is advanced through the combination of at least a puncturing balloon catheter having the above-described constitution, a puncturing needle equipped with an inner needle for guiding a guide wire on which roughening process or the like is performed for catching clearly an ultrasonic echo image for guiding a guide wire, a guide wire equipped with graduation and the like for tube introduction, a dilator equipped with a sheath for extending the puncture axes, and an indwelling catheter which indwells in stomach mainly via esophagus and effects drainage of digestive juices, infusion of drug solution and the like in which a balloon having an expanded diameter of 20 mm or more is placed at a position about 10 cm from the leading point and at least one side pore is provided on the catheter at the leading point side of the balloon, wherein each is enabled to be inserted even without endoscope or X-ray contrast.

Further, regarding use of the above-described medical tube inserting device of the present invention, specifically, a balloon catheter which does not rupture immediately even by needling is inserted to the puncture area via the nose and the like, a balloon is expanded by fluid such as physiological saline and the like, the balloon is needled by a puncturing needle aiming at a catheter shaft while externally confirming positions of the balloon and the catheter shaft using an ultrasonic probe, a guide wire is inserted into the balloon through the puncturing needle while confirming sure puncturing through transmission of movement to the shaft and outflow of fluid in the balloon from the end of the puncturing needle thereby ensuring lumen by the above-described balloon; the puncturing needle is pulled out, the balloon catheter for puncturing is proceeded further toward the anal area to forcibly direct the leading point of the guide wire toward anus side and the catheter is retained in the intended area, the puncture area is extended by a dilator equipped with a sheath, the dilator is pulled out, an indwelling catheter equipped with a balloon is inserted via the sheath and the balloon is expanded in the stomach and the like. After pulling the catheter, the operation is fixed to the esophago-cardiac junction for indwelling of the catheter in the intended area and ensuring a route for drainage of digestive juices and infusion of a medical solution and the like. By using the indwelling catheter equipped with a balloon constituted as described above, when, for example, the balloon is expanded in stomach and pulled toward the vicinity of the mouth, the above-described balloon is fixed to the esophago-cardiac junction of the stomach and the leading point of the indwelling catheter can be allowed to indwell at the fundus of the stomach irrespective of a differential in distance between the puncture area and the cardiac region of the stomach between individuals.

BRIEF DESCRIPTION OF THE DRAWINGS

FIG. 1 is a side view of a balloon catheter for puncturing which is one example of the present invention, FIG. 2 is an enlarged left side view of FIG. 1, FIGS. 3A to 3E are views showing a medical tube inserting device of the present invention, using method and using condition thereof.

BEST MODE FOR CARRYING OUT THE INVENTION

Figure 3A:
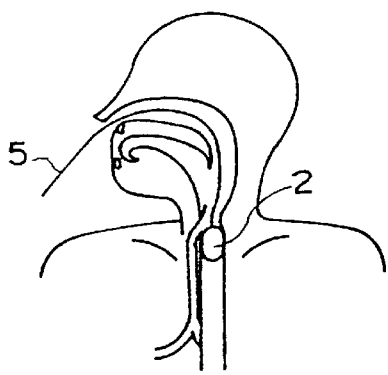
FIG. 3F is a view showing condition in which a conventional balloon which ruptures in puncturing is needled.

A balloon catheter (5) for puncturing of the present invention is constituted of a catheter shaft (1), a balloon (2), and a connector (3) as shown in FIG. 1. The catheter shaft (1) has a leading point which has been made round, one or more lumens, one of which is a lumen (4) for expanding a balloon and leading point thereof is closed, and has a side pore opening in balloon lumen. Separately, a guide wire may be inserted, or lumen may also be made for infusion of a medical solution and allowed to open in the leading point of a tube. The catheter shaft (1) is so formed as to have a length and a width corresponding to the physical constitution of a patient and the intended organ as well as position, and in the case of insertion via nose, the length is from 1 to 3 m and the width is from 2 to 6 mm, and in the case of insertion via anus likewise, the length is from 1 to 2 m and the width is from 4 to 6 mm, and in the case of insertion via urethra, the length is from 50 cm to 1 m and the width is from 1 to 3 mm. The catheter shaft has appropriate flexibility and elasticity at usual room temperature and body temperature, and as a material for forming the shaft, synthetic resins, for example, a soft vinyl chloride resin, polyurethane resin, silicone rubber and the like are usually suitably used, however, they are not limited examples, and it is more desirable that transmission of ultrasound is more different as compared with fluid in physiological saline and the like in the balloon (2). Further, it is also preferable that graduation (21) which measures insertion into the intended area is provided on the catheter shaft (1).

The balloon (2) is so formed that it has a length of 1 to 20 cm, an expanded diameter of 5 to 200 mm, and a thickness of 0.01 to 1 mm depending on the intended organ and position of insertion. For example, in the case of insertion via the nose, the balloon thickness is set as low as possible so that the balloon is not bulky; therefore, the thickness is from 0.1 to 0.3 mm, and in the case of use in the esophagus, the length is from 3 to 10 cm and the expanded diameter is about 30 mm, and in the case of use in the stomach, the length is from 5 to 20 cm and the expanded diameter is about 200 mm. Further, the material of the balloon is usually selected from synthetic resins having a JISA hardness of 20 to 80°, a tensile strength of 8 to 25 MPa, a tear strength of 20 to 60 kg/cm, a 100% modulus of 3 to 6 MPa, an elongation of 300 to 460% and a balloon internal pressure of 2.8 to 75 psi. For example, a soft vinyl chloride resin, polyurethane resin, silicone rubber and the like are usually suitably used, however, they are not limited examples, and polyethylene, polyester, natural rubber latex and the like may also be permissible.

However, in the case of use of silicone rubber, natural rubber latex and the like, there may be a possibility that a balloon ruptures immediately when needled by a puncturing needle due to its elasticity, there may also be countermeasures that a synthetic resin is impregnated or laminated on a nylon mesh and the like, or a synthetic resin is coated to form multiple layers on the surface or rear surface thereof so that a balloon does not rupture immediately when needled by a puncturing needle. For example, when a balloon of a balloon catheter inserted into the esophagus via the nose is made of a soft vinyl chloride resin, a material having a hardness of 60°, a tensile strength of 16 MPa, a tear strength of 45 kg/cm, a 100% modulus of 4.5 MPa and an elongation of about 400% is selected, the balloon is so made that the balloon thickness is from about 0.1 to 0.3 mm and the outer diameter is about ⅔ of desired expanded diameter; consequently, as the balloon is expanded to reach a desired expanded diameter, the esophageal catheter equipped with an inner needle lumen is secured and subsequently, when the puncturing needle is inserted into the balloon and the inner needle is pulled out, a suitable inner pressure is obtained so that fluid for expanding the balloon flows out from the needle end by internal pressure in the balloon. The balloon is molded into a desired form by blow molding, clip molding, extrusion molding, compression molding and the like.

The connector (3) desirably has lure taper so that it is connected to a syringe to ensure infusion of liquid for expanding a balloon and medical solution may be conducted, and depending on the case, it may also be allowable that plug members (one-way valve, two-way turn cock, three-way turn cock and the like) are used; and further, a connector having an end which can be locked may also be used and a pilot balloon for confirming expanded condition of a balloon is provided. The raw materials of the connector and the plug members are not particularly restricted, and synthetic resins such as a hard vinyl chloride resin, polycarbonate resin, ABS resin and the like may advantageously be used.

As shown in FIGS. 3A to 3E and FIG. 4, an indwelling catheter (11) can be retained safely and infallibly by the balloon catheter (5) for puncturing, an ultrasonic probe (6), a puncturing needle (7), a guide wire (8), a dilator (9), a sheath (10) and an indwelling catheter (11).

As an example of a method for use of a tube inserting device of the present invention, a method for making a percutaneous route for drainage of digestive juices, infusion of a medical solution, enteral nutrition and the like from the cervix to the stomach is shown below.

As shown in FIG. 3A, the balloon catheter (5) is inserted via the nose, the balloon (2) is expanded through the esophageal orifice to ensure lumen, and further the catheter (5) is pulled to ensure lumen of the cervical esophagus sufficiently which may be needled; the position of the balloon (2) is thereby confirmed by the ultrasonic probe (6).

Figure 4:
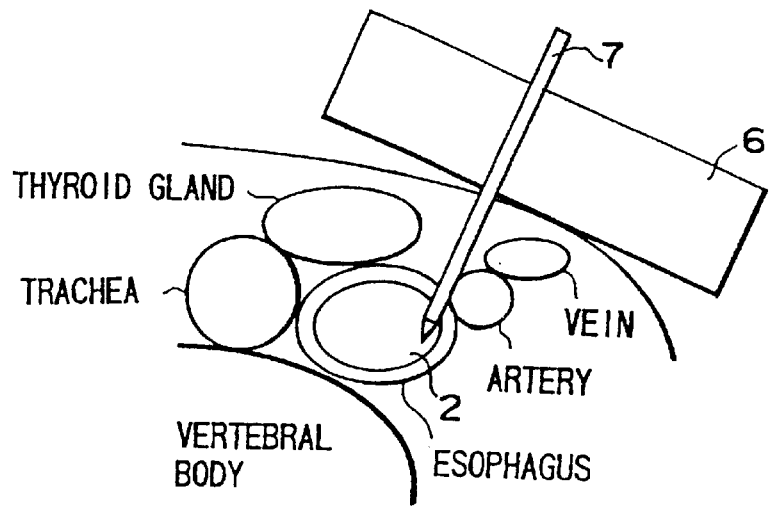
FIG. 4 is a schematic view showing a condition in which an ultrasonic probe is applied in puncturing.
Figure 5A:
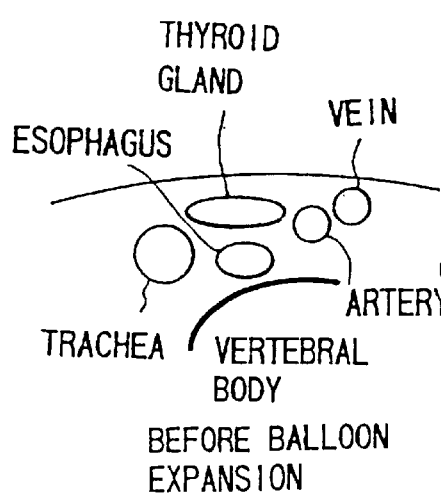
FIGS. 5A and 5B are schematic views showing ultrasonic echo images before and after expansion of a balloon of a balloon catheter.
Figure 5B:
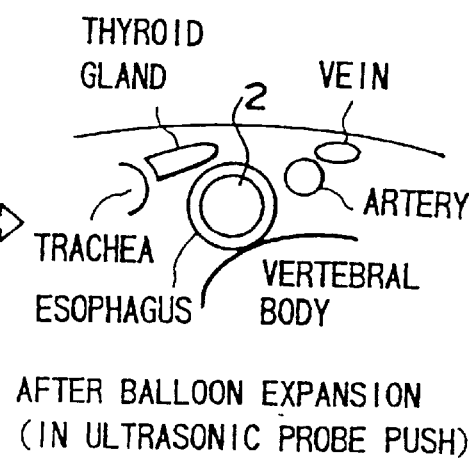

FIG. 4 is a schematic view showing a condition in which the ultrasonic probe (6) is applied in puncturing, and under this condition, the balloon (2) for puncturing is sandwiched between the ultrasonic probe (6) and a cervical vertebral body, the ultrasonic probe (6) is pushed strongly to move the thyroid gland, trachea, artery, vein and the like aside from the balloon (2) so that there is no danger of puncturing of organs between the predetermined puncturing position of skin and the balloon (2) for puncturing and to ensure the distance between the skin and the balloon (2) is minimized. Under this condition, the puncturing needle (7) is needled aiming at the balloon (2). FIGS. 5A and 5B are schematic views showing ultrasonogram images before and after expansion of the balloon of the balloon catheter (5).

As described above, in use of a tube inserting device of the present invention, space for needling of the puncturing needle (7) is secured by internal force of expansion of the balloon (2) in the esophagus and external force of a strong push of the ultrasonic probe (6).

Figure 3B:
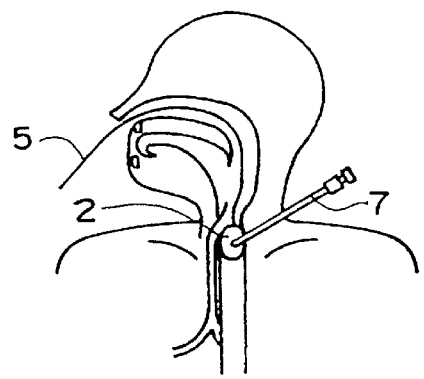

The ultrasonic probe (6) is pushed strongly while checking the balloon (2) to confirm that the puncturing operation is safe before the puncturing needle (7) is needled aiming at the balloon (2) and the catheter shaft (1) in the balloon (2) (see, FIG. 3B). Once the puncturing needle (7) is needled, the balloon (2) does not rupture; therefore, it is confirmed that the leading point of the puncturing needle (7) is present in the balloon and desirably is in contact with the catheter shaft (1) by the ultrasonogram images. Further, if the puncturing needle (7) branches to an inner needle and an outer needle, the inner needle is pulled out, and the leading tip of the puncturing needle (7) is needled into the balloon which is confirmed by an outflow of fluid for expanding a balloon due to balloon inner pressure from the end of the puncturing needle (7) positioned outside as shown in FIG. 3E. Therefore, in the case of a balloon made of a conventional material which ruptures, the balloon immediately ruptures in needling as exemplified in FIG. 3F, and can not accomplish the above-described function of a balloon of a balloon catheter of the present invention.

Figure 3C:
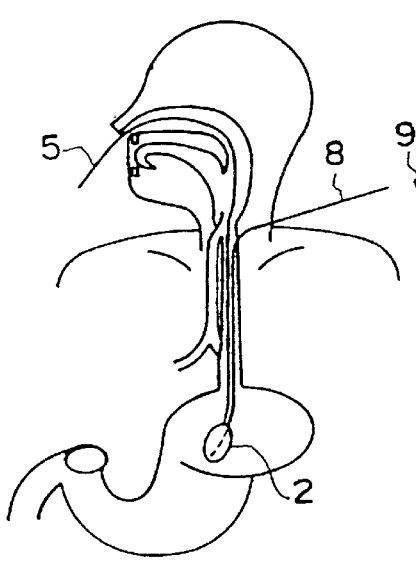

Then, the guide wire (8) is inserted into the balloon to a required extent from the end of the puncturing needle (7) as shown in FIG. 3C and the puncturing needle (7) is pulled out. The balloon catheter (5) is pushed in toward the anal area after deflating to direct the leading point of the guide wire (8) toward the anal area and is removed from the balloon to retain the guide wire (8) in the stomach or the esophagus.

The balloon catheter (5) is then pulled out from body. The dilator (9) equipped with the sheath (10) is inserted from the end of the guide wire (8), the puncture area is extended, and the dilator (9) is singularly pulled out.

Figure 3D:
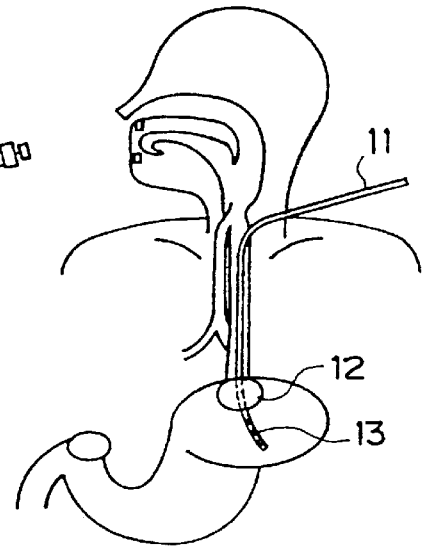
Figure 3E:
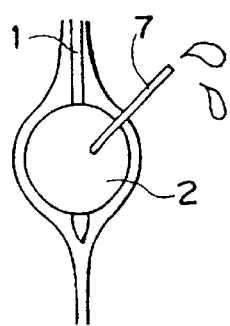
Figure 3F:
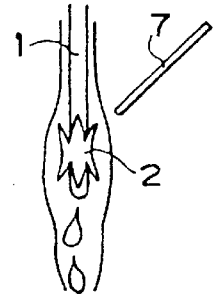

Further, the indwelling catheter (11) is inserted from the end of the guide wire as shown in FIG. 3D and inserted into body through inside the sheath (10). When the indwelling catheter (11) reaches inside the stomach, then the guide wire (8) and the sheath (10) are pulled out and the end of the indwelling catheter (11) is connected for use to a drainage bag, wherein the bag contains a enteral nutrition or medical solution or the like.

In the case of a method for making a percutaneous route for drainage of digestive juices, infusion of a medical solution, enteral nutrition and the like from the cervix to the stomach, the puncturing needle (7) may have no inner needle and may have a size of 18 G or the puncturing needle may have a combination of an inner needle and an outer needle as described above and a tubular needle so that fluid for expanding the balloon flows out of the needle end when the balloon (2) is needled or so that the guide wire (8) may be inserted. The leading point of a needle may be cut slantwise or a Huber-pointed needle may be devised so that the front edge is situated at the center of the leading point of a needle, and may be a needle of which the leading point has been subjected to a roughening process or grooving process so that a position can be confirmed easily by the ultrasonic probe (6). As a raw material thereof, stainless steel is usually used.

The guide wire (8) may have any specification providing it has a size of 0.035 inches and can pass through the lumen of the puncturing needle (7). It is preferable to provide graduation thereon so that secure insertion from a puncturing position into an indwelling position may be confirmed.

Since the dilator (9) extends from 10 Fr to 14 Fr, several dilators (9) having different diameters may be used or a stepped dilator (9) or several dilators (9) may be combined. Synthetic resins, such as a vinyl chloride resin, fluorine resin and the like are used as raw materials thereof.

The sheath (10) is formed so that it has a size of 16 Fr and has internal diameter into which the dilator (9) and the indwelling catheter can be inserted. The sheath may be a tubular article and it may be desirable that the sheath can be peeled off a fluorine resin having excellent sliding property and the like. Synthetic resins are used as a raw material thereof.

Figure 6:
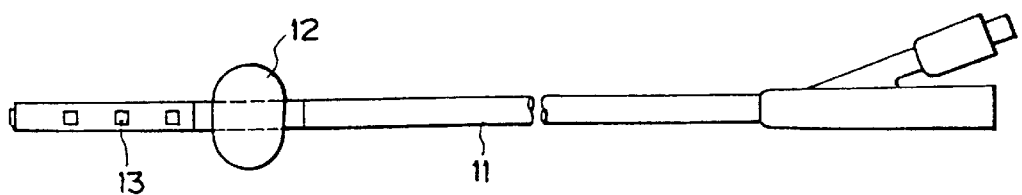
FIG. 6 is a side view of one example of an indwelling catheter.
Figure 7:
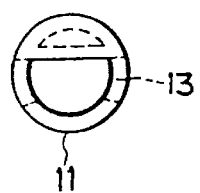
FIG. 7 is an enlarged left side view of FIG. 6.

As the indwelling catheter (11), a general drainage tube or nutrition tube may be used and it may be advantageous that the leading point area thereof reaching the indwelling position is made of a particularly soft material and has a form which does not injure organs. A side pore (13) may also be made as exemplified in FIG. 6 for enhancing the efficiencies of infusion and drainage.

Particularly in the case of an indwelling catheter retained in the stomach, a catheter having on the leading point a fixation balloon (12) which is expanded in the stomach before it is pulled and fixed at a cardiac region may also be permissible. There may also be envisaged use wherein when the balloon is constricted after a pulling operation and the leading point of the catheter is retained at an intended position. As raw materials, synthetic resins such as a vinyl chloride resin, silicone rubber and the like can be used, however, they are not limited examples.

Parts and methods to which the present invention is applied are not restricted to a method for making a percutaneous route for drainage of digestive juices, infusion of a medical solution, enteral nutrition and the like from the cervix to the stomach. Additionally, the indwelling catheter (11) can be percutaneously inserted safely into all hollow organs (esophagus, stomach, bile duct, pancreatic duct, intestine, urinary duct, urinary bladder and the like) but also by suitably changing sizes and raw materials of the balloon catheter (5), the puncturing needle (7), the guide wire (8), the dilator (9), the sheath (10) and the indwelling catheter (11) which are used.

INDUSTRIAL APPLICABILITY OF THE INVENTION

When a balloon catheter for puncturing and indwelling, a medical tube inserting device using this catheter, and a method for use thereof according to the present invention are used, a balloon of a balloon catheter does not rupture even if it is needed. Therefore, sufficient lumen can be secured at a puncturing position and a route for drainage of digestive juices, infusion of a medical solution, enteral nutrition and the like can be percutaneously made safely and surely in all hollow organs (esophagus, stomach, bile duct, pancreatic duct, intestine, urinary duct, urinary bladder and the like). Further, when a route for infusion of a enteral nutrition and the like using a conventional balloon catheter which ruptures immediately in puncturing, several medical personnel may be required in an operation room for use of an X-ray fluoroscopy and an endoscope; however, when a balloon catheter for puncturing which does not rupture and a medical tube inserting device of the present invention are used, a route for drainage of digestive juices, infusion of a medical solution, enteral nutrition and the like may be made at bed side by two persons, providing that ultrasonic diagnostic equipment is available.

What is claimed is:

1. A balloon catheter for puncturing comprising a balloon and a catheter which is inserted into a puncture area in a body via an orifice, expanded by a fluid to define a lumen and needled, wherein said balloon is so constituted than when it is needled percutaneously by a puncturing needle, it does not rupture immediately and the lumen can be ensured, wherein the balloon has a thickness of 0.01 to 1 mm, a tensile strength of 8 to 25 MPa, a tear strength of 20 to 60 kg/cm, a 100% modulus of 3 to 6 MPa, an elongation of 300 to 460% and a balloon internal pressure of 2.8 to 75 psi.

2. A balloon catheter for puncturing according to claim 1, wherein a catheter shaft part made of a material having remarkably different levels of ultrasound transmission as compared with the fluid in the balloon catheter, is placed approximately in an axial center of the lumen.

3. A balloon catheter for puncturing according to claim 1, wherein for improvement of insertion operation, the balloon catheter includes an internal catheter lumen so that the balloon catheter can be easily inserted in a hollow organ along a guide wire previously inserted in the hollow organ, said internal catheter lumen also capable of receiving a stilet for firming the balloon catheter.

4. A balloon catheter for puncturing according to claim 1, wherein for enabling insertion operation without X-ray contrast, graduation is provided on the catheter shaft and a fixation balloon for confirming expansion of the balloon is placed in the vicinity of a connection.

5. A balloon catheter for puncturing according to claim 1, wherein the balloon has an outer diameter substantially equal to ⅔ of a desired expanded diameter.

6. A medical tube inserting device constituted of a combination of at least a balloon catheter, a puncturing needle, a guide wire and an indwelling catheter, said balloon catheter comprising a balloon and a catheter for puncturing which is inserted into a puncture area in a body orifice expanded by a fluid to define a lumen and needled, wherein said balloon is so constituted than when it is needled percutaneously by the puncturing needle, it does not rupture immediately and the lumen can be ensured, wherein the balloon has a thickness of 0.01 to 1 mm, a tensile strength of 8 to 25 MPa, a tear strength of 20 to 60 kg/cm, a 100% modulus of 3 to 6 MPa, an elongation of 300 to 460% and a balloon internal pressure of 2.8 to 75 psi; said puncturing needle with a roughen exterior for creating an ultrasonic echo image for guiding the guide wire, the guide wire equipped with a sheath for extending into the puncture area, wherein said puncturing needle is enabled to be inserted even without endoscope or X-ray contrast by using an ultrasonic diagnostic equipment.

7. A medical tube inserting device according to claim 6, wherein the indwelling catheter is a catheter which indwells in stomach via an esophagus and effects draining of digestive juices, infusion of drug solution in which a fixation balloon having an expanded diameter of 20 mm or more is placed at a position about 10 cm from the leading point and at least one side pore is provided on the indwelling catheter at the leading point side of the balloon.

8. A balloon according to claim 1, wherein the balloon is constructed from soft vinyl chloride, polyurethane resin, polyethylene, polyester, silicon rubber, or natural rubber latex.

9. A balloon according to claim 8, wherein the balloon is constructed silicon rubber which is impregnated in or laminated on a nylon mesh.

10. A method for use of a medical tube inserting device, comprising the steps of:

provoding a balloon catheter comprising a balloon and a catheter, wherein the balloon having a thickness of 0.01 to 1 mm, a tensile strength of 8 to 25 MPa, a tear strength of 20 to 60 kg/cm, a 100% modulus of 3 to 6 MPa, an elongation of 300 to 460% and a balloon internal pressure of 2.8 to 75 psi, enabling said balloon not to rupture immediately when needed;

inserting said balloon catheter via a body orifice;

positioning said balloon proximate to the puncture area;

expanding the balloon by a fluid;

aiming a puncturing needle at a catheter shaft while externally confirming position of the balloon and the catheter shaft using an ultrasonic probe;

needling the balloon with the puncturing needle;

inserting a guide wire into the balloon through the puncturing needle while confirming needling of said balloon by an outflow of the fluid in the balloon from an end of the puncturing needle;

removing the puncturing need from the puncture area;

extending the balloon further past the puncture area while retaining the guide wire in an intended area;

expanding the puncture area with a dilator equipped with a sheath;

removing the dilator while retaining the sheath within the puncture area;

inserting an indwelling catheter via the guide wire; and, retaining the indwelling catheter via the sheath;

thereby securing a route via the indwelling catheter for draining of digestive juices or for infusion of medical solutions.

\* \* \* \* \*